United States Patent [19]
Gregory

[11] 4,162,677
[45] Jul. 31, 1979

[54] CRYOGENIC DEVICE AND METHOD FOR NECROTIZING AND SHAVING LIVE TISSUE

[75] Inventor: Harold D. Gregory, West Covina, Calif.

[73] Assignee: Virginia M. Gregory, West Covina, Calif.

[21] Appl. No.: 798,364

[22] Filed: May 19, 1977

[51] Int. Cl.$^2$ .................................... A61B 17/36
[52] U.S. Cl. .................... 128/303.1; 62/50; 62/78; 62/514 R; 128/1 R; 220/20.5
[58] Field of Search ............... 128/303.1, 400, 1 R, 128/DIG. 27; 62/50, 78, 293, 514 R, 45; 220/20.5, 23, 3.1

[56] References Cited
U.S. PATENT DOCUMENTS

| 3,080,725 | 3/1963 | Cowley et al. | 62/62 |
| 3,736,937 | 6/1973 | Basiulis | 128/303.1 |
| 3,748,865 | 7/1973 | Laverman et al. | 62/50 |

*Primary Examiner*—Robert W. Michell
*Assistant Examiner*—Michael H. Thaler
*Attorney, Agent, or Firm*—Sellers and Brace

[57] ABSTRACT

A hand-held cryogenic device for and method of necrotizing and shaving live tissue having a chamber chargeable with liquid cryogen. One heat conductive wall of the chamber is adapted to be flooded with cryogen while being manipulated over the tissue and includes an opening allowing gaseous cryogen to escape in contact with the tissue. This wall is selectively effective to shave or slice away necrotized tissue.

16 Claims, 3 Drawing Figures

CRYOGENIC DEVICE AND METHOD FOR NECROTIZING AND SHAVING LIVE TISSUE

This invention relates to cryogenic devices, and more particularly to a self-contained hand-held cryogen storage chamber having one wall adapted to be flooded with cryogen when inverted and held against tissue to be necrotized and includes means for shaving away necrotized tissue as the device is manipulated thereover.

Many proposals have been made heretofore for devices utilizing cryogenic fluids to necrotize live tissue both by jetting the cryogen directly onto the tissue or by utilizing the fluid to cool a heat conductive probe held in contact with the tissue. Typical prior art cryogenic devices of this type are disclosed in Kanbar et al. U.S. Pat. Nos. 3,259,131, 3,425,417; Allen U.S. Pat. Nos. 3,536,076, 3,795,245; Katz U.S. Pat. No. 3,270,744; and Basiulis U.S. Pat. No. 3,736,936. Each of these devices comprises a self-contained hand-held unit chargeable with a limited supply of cryogen metered onto one end of a heat conductive probe remote from the probe end in contact with tissue undergoing treatment. Separate openings are provided to charge the cryogen reservoir and to vent gaseous cryogen to the atmosphere with the tissue. Each lacks any provision for venting the gaseous cryogen over the surface undergoing cooling and utilizing the substantial cooling benefits available therefrom.

The foregoing and other shortcomings of prior cryogenic devices are avoided by this invention which is characterized by its extreme simplicity, versatility, effectiveness and capability of shaving away thin slices of necrotized tissue. Typically, the device comprises a cryogen reservoir major portions of which are heat insulated and another large area wall of which is uninsulated and adapted to be flooded with cryogen while held pressed against tissue to be necrotized. The latter surface is provided with a combined charging opening and escape port for gaseous cryogen which escapes along the interface between the exterior of the uninsulated wall and the tissue undergoing treatment. When not in use the device is up-ended to store the cryogen in the insulated portion of the reservoir and the escape port is closed by a ported insulated closure. The edge of the charging opening functions to shave away necrotized tissue in a thin film when the pressure against the tissue is increased slightly whereas it remains substantially uneffective to shave tissue when passed lightly over the tissue. The device is particularly advantageous in treating larger areas of tissue as for example skin afflicted with a variety of skin diseases such as acne, excema, etc.

Accordingly, it is a primary object of this invention to provide a unique cryogenic device for necrotizing live tissue while a heat conducting wall flooded with liquid cryogen is held against or manipulated over the tissue to be treated.

Another object of the invention is the provision of a hand-held self-contained cryogen device containing a quantity of liquid cryogen having a heat conducting wall adapted to be held against tissue to be necrotized and having an opening through which cryogen gas escapes in direct contact with tissue undergoing treatment.

Another object of the invention is the provision of a hand-held cryogen device having a relatively thin heat conducting wall adapted to be held in contact with tissue undergoing cooling and provided with an edge effective to shave away a thin slice of necrotized tissue.

Another object of the invention is the provision of a self-contained hand-held cryogenic device having a large area heat conductive surface designed to be held in direct contact with tissue while necrotizing the same and having an opening therethrough suitable for the dual purpose of charging the device with cryogen and providing an escape passage for gaseous cryogen.

These and other more specific objects will appear upon reading the following specification and claims and upon considering in connection therewith the attached drawing to which they relate.

Referring now to the drawing in which a preferred embodiment of the invention is illustrated:

Figure 1:
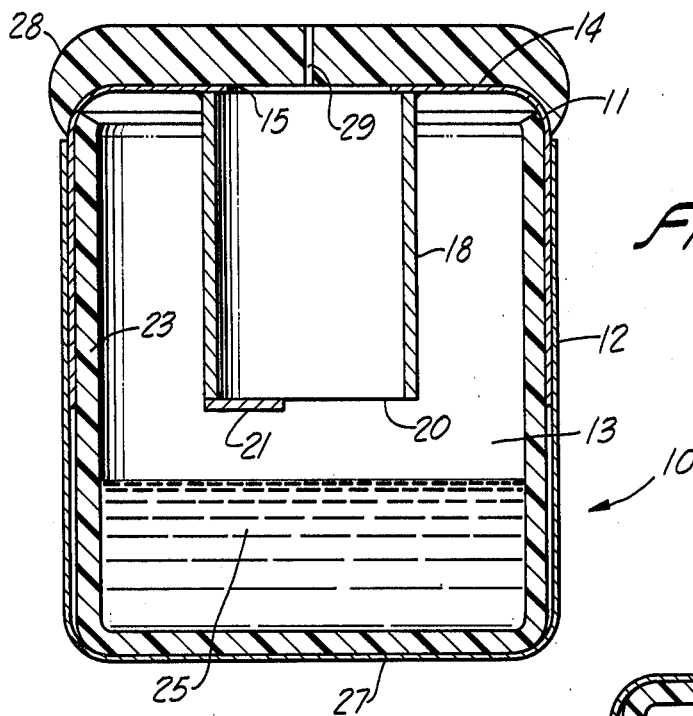
FIG. 1 is a cross-sectional view through an illustrative embodiment of the invention while positioned in an upright non-operating position.

Referring initially more particularly to FIG. 1, there is shown an illustrative embodiment of the invention cryogenic device, designated generally 10, having a generally cylindrical main housing sized for grasping in the operator's hand. As shown by way of example, this housing comprises two cup-shaped members 11 and 12 having their lip ends snugly telescoped together to form a storage chamber 13 for a quantity of liquid cryogen. Members 11 and 12 may be formed of any suitable metal and silver soldered or bonded together in a fluid-tight manner along the interface between their sidewalls. The bottom 14 of member 11 has a large opening 15 centrally thereof having multiple functions which will be described in greater detail presently.

A tubular sleeve 18 having an internal diameter somewhat greater than opening 15 is located within reservoir 13 and one end is soldered or otherwise secured to the interior bottom 14 adjacent the periphery of opening 15. The open inner end 20 of sleeve 18 terminates near the midsection of the reservoir and may be partially closed by a member 21 to safeguard against the accidental loss of cryogen while inverting the device 10 from a non-operating into an operating position.

The walls of reservoir 13, except bottom wall 14, are heat insulated as by a liner of insulation 23. Preferably, but not necessarily, this insulation liner 23 is located interiorly rather than exteriorly of the reservoir. The main body of the reservoir may be formed of stainless steel or the like metal to facilitate cleaning and sterilization of the device. Styrofoam or the like insulation material having an impervious skin provides excellent heat insulation.

Figure 2:
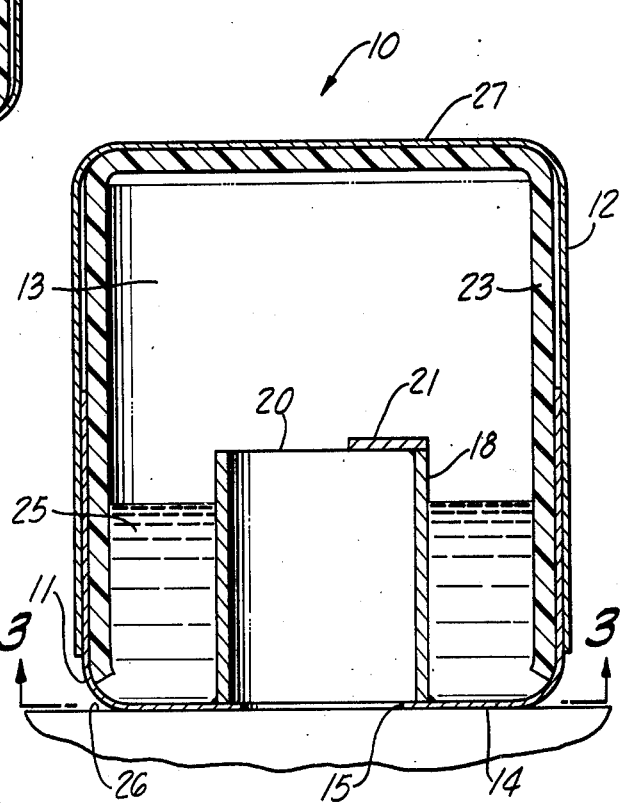
FIG. 2 is a cross-sectional view similar to FIG. 1 but showing the device inverted and positioned against tissue undergoing necrotizing.
Figure 3:
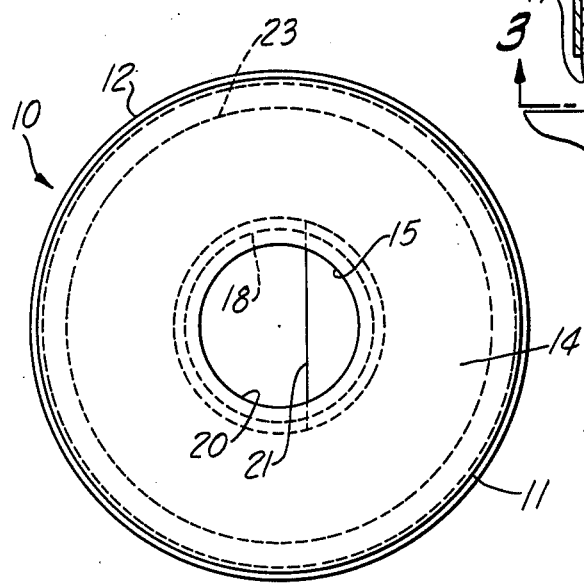
FIG. 3 is a view of the charging and venting end of the device taken along line 3—3 on FIG. 2.

In use, the surgeon first introduces a quantity of liquid cryogen, such as nitrogen 25, into reservoir 13, through opening 15 using any suitable charging device well known to workers skilled in this art. Thereafter, the surgeon upends or inverts device 10 to the operating position shown in FIG. 2. Sleeve 18 cooperates with the container walls in trapping the cryogen 25 and retaining all liquid portions thereof captive. Gaseous cryogen however flows downwardly through sleeve 18 and opening 15. The uninsulated and flooded flat bottom 14 of the device is placed directly against the tissue 26 to be necrotized as, for example, the skin of the patient suffering from acne, excema or one of many other skin maladies. Typically, the diameter of device 10 may be two to three inches so as to be readily grasped in the operator's hand opposite the heat insulating liner 23 while being manipulated over the particular area to be necrotized.

The direct contact of the metallic surface 14 with the tissue produces rapid cooling of the tissue by the liquid cryogen flooding the interior side of wall 14. Portions of this liquid are vaporized and this vapor escapes upwardly and then downwardly through sleeve 18 from which the vapor escapes through opening 15 and radially outward between the tissue 26 and the exterior surface of wall 14. This film of vapor or gas not only provides additional cooling but partially isolates the tissue from direct contact with the metal surface and also serves to minimize the resistance to movement of the device over the tissue. As the tissue necrotizes it becomes brittle and fragile and any necrotized cellular protuberances as well as a thin layer of the tissue itself may be shaved away by the outer rim edge of opening 15. This slicing or shaving action is readily controlled by the operator depending upon the manual pressure applied to device 10 as it is moved across the tissue being cooled.

Whenever the surgeon wishes to inspect the progress of the treatment he merely upends the device to the position shown in FIG. 1 without need for releasing his grasp of the device. When the device is upended as shown in FIG. 1, the liquid cryogen is out of contact with wall 14 with the result that the cryogen vaporizes at a relatively slow rate compared with the relatively high rate of vaporization occuring when the cryogen is in contact with wall 14 as it is in FIG. 2. Alternatively, of course the surgeon may place the imperforate end 27 of the device against a supporting surface while making a more extensive investigation of the area treated. During such periods of non-use bottom wall 14 is preferably capped with a loose fitting cap 28 of heat insulating material provided with a vent port 29. This closure is laid to one side during periods of use of device 10.

While the particular cryogenic device and method for necrotizing and shaving live tissue herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A cryogenic device for treating skin and/or live tissue cryogenically comprising:
    means providing a hollow storage chamber for liquid cryogen having a cryogen storing portion thereof heat insulated and adapted to store a cryogen charge when said device is not in use and having a metallic wall thereof adapted to be flooded on its interior with liquid cryogen while the exterior surface of said metallic wall is held in close heat exchange relation to tissue to be cooled; and
    means for conducting gaseous cryogen from said storage chamber through said metallic wall and discharging the same past the interface between the tissue undergoing cooling and said exterior surface of said metallic wall.

2. A cryogenic device as defined in claim 1 characterized in that said means for conducting gaseous cryogen from said storage chamber serves additionally as the cryogen charging passage for said device.

3. A cryogenic device as defined in claim 1 characterized in that said metallic wall includes means effective to shave off portions of tissue as said metallic wall is moved across and in contact with the tissue undergoing cooling.

4. A cryogenic device as defined in claim 3 characterized in that said metallic wall provides a wide area flat supporting surface surrounding said tissue shaving means and effective to limit the thickness of tissue shavings.

5. A cryogenic device as defined in claim 1 characterized in that the exposed exterior wall of said cryogen storage chamber is formed in major part of stainless steel embracing an impervious liner of heat insulating material for said cryogen storing portion thereof.

6. A cryogenic device as defined in claim 1 characterized in that said storage chamber comprises a pair of cup-shaped members the open ends of which have been telescoped together in a fluid-tight manner, the bottom of one of said members having an opening for the passage of cryogen, and a tubular member interiorly of said storage chamber having one end secured about said opening in a fluid-tight manner with its opposite inner end in communication with the interior of said chamber to convey gaseous cryogen therefrom.

7. A cryogenic device as defined in claim 6 characterized in that the inner end of said tubular member is located generally near the midlength of said storage chamber thereby to limit the quantity of liquid cryogen which can be stored therein when said device is positioned for use to treat tissue.

8. A cryogenic device as defined in claim 1 characterized in that said storage chamber has a second surface generally parallel to and remote from said metallic wall, said remote surface providing a broad surface for supporting said device in a stable position with said metallic wall uppermost and out of direct heat exchange with liquid cryogen.

9. A cryogenic device as defined in claim 1 characterized in that said device is self-contained and sized to be grasped in the user's hand and manipulated to glide said metallic wall over the area of tissue undergoing necrotizing by cryogen contained in said storage chamber.

10. That method of treating live tissue cryogenically which comprises:
    storing a quantity of liquid cryogen in a container having one end portion heat-insulated and adapted to be grasped in the user's hand with the other non-insulated heat-conducting end thereof underlying the user's hand and flooded with liquid cryogen and held pressed against live tissue to be cooled; and
    conducting gaseous cryogen from said container through said heat-conducting end and between the exterior of said heat-conducting end and the tissue being cooled thereby to utilize the cooling capacity of said gaseous cryogen.

11. That method of treating live tissue cryogenically which comprises:
    storing a quantity of liquid cryogen in a hand-held container having a major portion thereof heat-insulated and sized to be grasped in the user's hand and having a non-insulated heat transfer surface adapted to be held in heat absorbing contact with live tissue to be cooled;
    utilizing the transfer of heat through said heat transfer surface from live tissue in contact therewith to flash a portion of said liquid cryogen into gas; and conducting said gas phase cryogen through a passage opening through said heat transfer surface and along the interface between the tissue and said heat transfer surface to effect further cooling of the tissue.

12. That method defined in claim 11 characterized in the step of manipulating said container to maneuver the heat transfer surface thereof over different contiguous areas of the tissue while utilizing the end of said passage in contact with tissue to shave away a layer of the tissue.

13. That method defined in claim 11 characterized in the step of providing said container with a second surface remote from said heat transfer surface, and upending said container onto said second surface to support said container in a stable position when not in use to treat tissue.

14. That method defined in claim 11 characterized in the steps of utilizing a double-ended invertable container to store said liquid cryogen and one of which ends includes said heat transfer surface and the other of which is usable to support said container in a stable position with the liquid cryogen contents out of contact with said heat transfer surface.

15. That method defined in claim 11 characterized in the step of controlling vaporization of said liquid cryogen between a relatively fast rate and a relatively slow rate by reversing the upright position of said container from a first position wherein the liquid cryogen contacts said heat transfer surface and a position wherein the liquid is confined to the heat insulated portion thereof.

16. That method defined in cliam 11 characterized in the step of providing said heat transfer surface with a tissue-shaving edge effective to shave a layer of tissue in contact therewith as said container is moved in a direction to advance said edge in a shaving direction but which edge is ineffective to shave tissue when moved in the opposite direction.

* * * * *